United States Patent

Takesue et al.

[11] Patent Number: 5,721,082
[45] Date of Patent: Feb. 24, 1998

[54] ELECTROPHOTOGRAPHIC PHOTORECEPTOR CONTAINING AMINE COMPOUND

[75] Inventors: Atsushi Takesue; Mitsutoshi Anzai; Takanobu Watanabe; Chieko Inayoshi, all of Kanagawa, Japan

[73] Assignee: Hodogaya Chemical Co., Ltd., Kawasaki, Japan

[21] Appl. No.: 429,902

[22] Filed: Apr. 27, 1995

[30] Foreign Application Priority Data

Oct. 31, 1994 [JP] Japan .................... 6-288629

[51] Int. Cl.[6] ............................................. G03G 5/06
[52] U.S. Cl. ............................ 430/73; 430/71; 430/72; 430/59
[58] Field of Search ........................... 430/71, 73, 72, 430/59

[56] References Cited

U.S. PATENT DOCUMENTS

| | | | |
|---|---|---|---|
| 4,111,693 | 9/1978 | Wright et al. | 430/73 |
| 4,515,883 | 5/1985 | Sasaki | 430/73 |
| 4,603,097 | 7/1986 | Shoshi et al. | 430/73 |
| 4,859,556 | 8/1989 | Sasaki . | |
| 4,892,949 | 1/1990 | Sasaki . | |

FOREIGN PATENT DOCUMENTS

| | | |
|---|---|---|
| 34 5466 | 6/1956 | Japan . |
| 52-4188 | 2/1977 | Japan . |
| 55-42380 | 10/1980 | Japan . |
| 56-123544 | 9/1981 | Japan . |
| 58-32372 | 7/1983 | Japan . |
| 61-40104 | 9/1986 | Japan . |
| 62-30255 | 2/1987 | Japan . |
| 62-35673 | 8/1987 | Japan . |
| 63-18738 | 4/1988 | Japan . |
| 63-19867 | 4/1988 | Japan . |
| 63-35976 | 7/1988 | Japan . |
| 3 39306 | 6/1991 | Japan . |
| 4-321649 | 11/1992 | Japan . |

OTHER PUBLICATIONS

English translation of JP 4–321649, Nov. 1992.
Schaffert, R. M. Electrophotography. New York: John Wiley & Sons, pp. 63–65, 1975.
Diamond, Arthur S., editor. Handbook of Imaging Materials. New York: Marcel–Dekker, Inc. pp. 424–426, 1991.
Chemical Abstracts 120:19182 (1992).

*Primary Examiner*—Christopher D. Rodee
*Attorney, Agent, or Firm*—Oblon, Spivak, McClelland, Maier & Neustadt, P.C.

[57] ABSTRACT

There are provided an electrophotographic photoreceptor having a photosensitive layer containing at least one amine compound represented by formula (1):

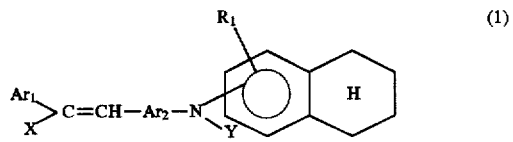

wherein $Ar_1$ represents a substituted or unsubstituted aryl group; $Ar_2$ represents a substituted or unsubstituted phenylene group, a substituted or unsubstituted naphthylene group, a substituted or unsubstituted biphenylene group or a substituted or unsubstituted anthrylene group; $R_1$ represents a hydrogen atom, a lower alkyl group or a lower alkoxy group; X represents a hydrogen atom, a substituted or unsubstituted alkyl group, or a substituted or unsubstituted aryl group; and Y represents a substituted or unsubstituted aryl group, or a group represented by formula (2) or (3) described in the specification.

10 Claims, 2 Drawing Sheets

ELECTROPHOTOGRAPHIC PHOTORECEPTOR CONTAINING AMINE COMPOUND

FIELD OF THE INVENTION

The present invention relates to an electrophotographic photoreceptor having a photosensitive layer containing a specific amine compound.

BACKGROUND OF THE INVENTION

Electrophotography is a kind of image-forming process, which generally comprises charging the surface of a photoreceptor containing a photoconductive material in the dark by means of, e.g., corona discharge, image-wise exposing the resulting photoreceptor to selectively eliminate the charge in the exposed area to thereby obtain an electrostatic latent image, converting the latent image into a visible image using a toner, transferring the toner image to paper, etc., and then fixing the toner particles to obtain an image.

Photoreceptors include inorganic photoreceptors containing an inorganic photoconductive compound, e.g., selenium, zinc oxide, cadmium sulfide, or silicon, as a major component and organic photoreceptors containing an organic charge generation material and a low- or high-molecular organic charge transporting material both of which are dispersed in a binder resin. The inorganic photoreceptors each has many advantages and has been widely used so far. However, those inorganic photoconductive compounds have the following drawbacks. For example, selenium not only is costly because of the difficulty of the production thereof, but also tends to crystallize and to be readily affected by heat or mechanical shock to thereby suffer performance deterioration. Zinc oxide and cadmium sulfide are insufficient in moisture resistance and mechanical strength, and a dye added as a sensitizer is deteriorated by the charging and exposure. Thus, photoreceptors containing zinc oxide or cadmium sulfide are defective in durability, etc. Silicon is also costly because of the difficulty of the production thereof and because a highly irritant gas is used for producing the same. Moreover, care should be taken in handling silicon because it is sensitive to moisture.

For the purpose of overcoming the drawbacks of these inorganic photoreceptors, organic photoreceptors containing various organic compounds have been investigated in recent years and have come to be used widely. The organic photoreceptors include single-layer photoreceptors in which both a charge generation material and a charge transporting material are dispersed in a binder resin and double-layered photoreceptors which comprise a charge generation layer and a charge transporting layer which layers perform their respective functions. Organic photoreceptors of the double-layer type are advantageous in that each material can be selected from a wide range of compounds and a photoreceptor having a desired performance can be produced relatively easily by selecting a suitable material combination. Because of this, a large number of investigations have been made on double-layered organic photoreceptors, which are in wide use.

As the charge generation materials, various kinds of organic pigments and dyes have been proposed and put to practical use. Examples thereof include azo compounds, bisazo compounds, trisazo compounds, tetrakisazo compounds, thiapyrylium salts, squarilium salts, azulenium salts, cyanine dyes, perylene compounds, metal-free or metal phthalocyanine compounds, polynuclear quinone compounds, thioindigo compounds, and quinacridone compounds.

Examples of charge transporting materials include the oxadiazole compounds disclosed in JP-B-34-5466, the oxazole compounds disclosed in JP-A-56-123544, pyrazoline compounds disclosed in JP-B-52-41880, the hydrazone compounds disclosed in JP-B-55-42380, JP-B-61-40104, JP-B-62-35673, and JP-B-63-35976, the diamine compounds disclosed in JP-B-58-32372, stilbene compounds disclosed in JP-B-63-18738, JP-B-63-19867, and JP-B-3-39306, and the butadiene compounds disclosed in JP-A-62-30255. (The terms "JP-B" and "JP-A" as used herein mean an "examined Japanese patent publication" and an "unexamined published Japanese patent application," respectively.) Some of the organic photoreceptors containing these charge transporting materials have excellent properties and have come into practical use. However, any organic photoreceptor has not been obtained so far which fully satisfies the various property requirements which an electrophotographic photoreceptor is required to meet.

A charge transporting material for use in an organic photoreceptor is required not only to enable the photoreceptor to satisfy various property requirements as a photoreceptor including sensitivity, but also to have chemical stability so as to withstand light, ozone, and electrical load and further have stability or durability so as not to cause a sensitivity decrease even when the photoreceptor is used repeatedly or over long.

SUMMARY OF THE INVENTION

An object of the present invention is to provide an electrophotographic photoreceptor having satisfactory photoreceptor properties and high sensitivity and durability.

The present invention provides an electrophotographic photoreceptor having a photosensitive layer containing at least one amine compound represented by formula (1):

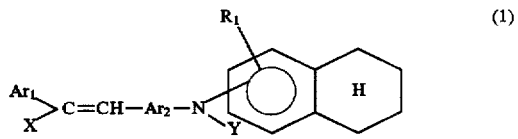

wherein $Ar_1$ represents a substituted or unsubstituted aryl group; $Ar_2$ represents a substituted or unsubstituted phenylene group, a substituted or unsubstituted naphthylene group, a substituted or unsubstituted biphenylene group or a substituted or unsubstituted anthrylene group; $R_1$ represents a hydrogen atom, a lower alkyl group or a lower alkoxy group; X represents a hydrogen atom, a substituted or unsubstituted alkyl group, or a substituted or unsubstituted aryl group; and Y represents a substituted or unsubstituted aryl group, or a group represented by formula (2) or (3):

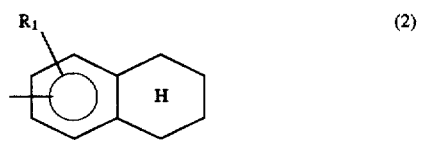

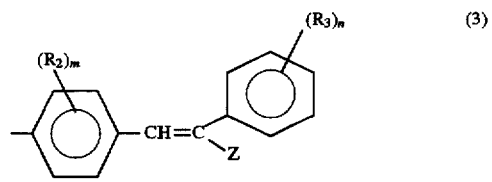

wherein $R_1$ is as defined above; $R_2$ represents a hydrogen atom, a lower alkyl group or a lower alkoxy group; $R_3$ represents a hydrogen atom, a halogen atom or a lower alkyl group; Z represents a hydrogen atom or a substituted or unsubstituted aryl group; and m and n each represents an integer of 0 to 4.

DETAILED DESCRIPTION OF THE INVENTION

Figure 1:
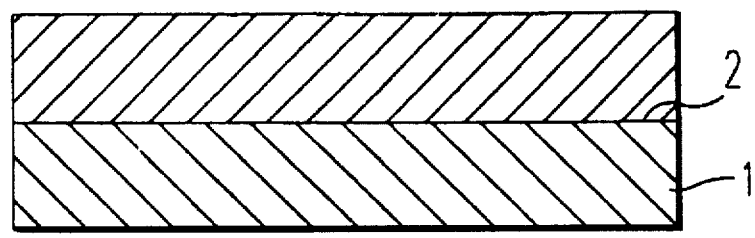
FIG. 1 is a sectional view of a single-layer electrophotographic photoreceptor.

The amine compound represented by formula (1) will be described in more detail below.

The amine compound represented by formula (1) described above, which is contained in the photosensitive layer in the present invention, is a novel compound. This compound may be synthesized from a corresponding amino compound by N-arylating the amino compound generally by, e.g., the Ullmann reaction to synthesize a triarylamine compound, formylating the triarylamine compound, and reacting the formylated compound with a corresponding phosphonic ester by the Wittig-Honer-Emmons reaction. The formylation is generally conducted by the Vilsmeier reaction.

For example, a diarylamine compound represented by formula (4):

$$Ar_2\text{—NH—Y} \tag{4}$$

(wherein $Ar_2$ and Y have the same meanings as in formula (1) described above ) is condensed with a halogenated tetralin compound represented by formula (5):

(wherein $R_1$ has the same meaning as in formula (1) described above and A represents a chlorine atom, a bromine atom, or an iodine atom) to obtain a triarylamine compound represented by formula (6):

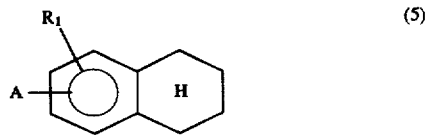

(wherein $Ar_2$, $R_1$, and Y have the same meanings as in formula (1) described above). This triarylamine compound is formylated with N,N-dimethylformaldehyde and phosphorus oxychloride or the like to obtain an aldehyde compound represented by formula (7):

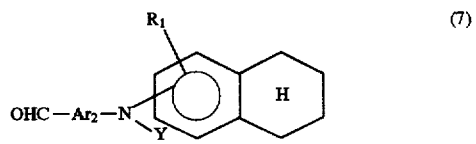

(wherein $Ar_2$, $R_1$, and Y have the same meanings as in formula (1) described above).

This aldehyde compound is then reacted with a phosphonic ester represented by formula (8):

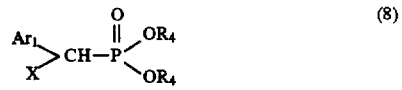

(wherein $Ar_1$ and X have the same meanings as in formula (1) described above and $R_4$ represents a lower alkyl group) to obtain the amine compound represented by formula (1) of the present invention.

In the case where the amine compound of the present invention is represented by the above-described formula (1) wherein Y is represented by formula (12):

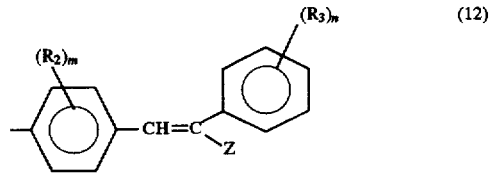

(wherein $R_2$, $R_3$, Z, n, and m have the same meanings as in formula (1) described above), this amine compound may be obtained from an N-arylaniline compound represented by formula (9):

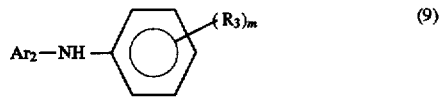

(wherein $Ar_2$, $R_2$, and m have the same meanings as in formula (1) described above) by subjecting the N-arylaniline compound to a condensation reaction and a formylation reaction in the same manner as described above to synthesize an amine compound represented by formula (10):

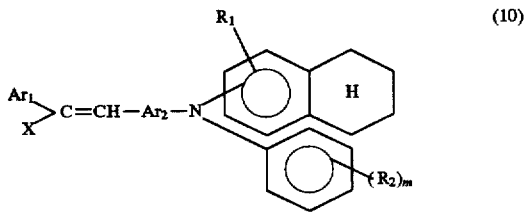

(wherein $Ar_1$, $Ar_2$, $R_1$, $R_2$, X, and m have the same meanings as in formula (1) described above), formylating the amine compound, and then reacting the formylated compound with a phosphonic ester represented by formula (11):

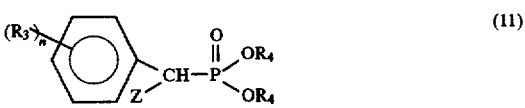

(wherein $R_3$, $R_4$, Z, and n have the same meanings as in formula (1) described above).

The amine compound of the present invention may also be synthesized from either an arylaminotetralin compound represented by formula (13):

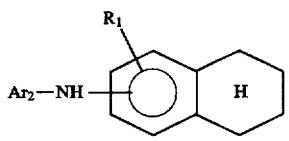

(wherein Ar$_2$ and R$_1$ have the same meanings as in formula (1) described above) or a tetralin compound represented by formula (14):

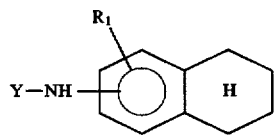

(wherein R$_1$ and Y have the same meanings as in formula (1) described above) by subjecting the starting compound to an arylation reaction, a formylation reaction and a condensation reaction in the same manner as described above.

The condensation reaction of the aforementioned diarylamine compound with the aforementioned halogenated tetralin compound or the like is known as the Ullmann reaction; this reaction is carried out either without or in the presence of a solvent. A high-boiling solvent, e.g., nitrobenzene, dichlorobenzene, or dimethyl sulfoxide, may be used as the solvent. Potassium carbonate, sodium carbonate, sodium hydrogen carbonate, potassium hydroxide, sodium hydroxide, or the like may be used as a deacidifying agent. A catalyst such as a copper powder or a copper halide is generally used to conduct the reaction. The reaction temperature is generally from 160° to 230° C.

The condensation reaction of the aforementioned aldehyde compound with the aforementioned phosphonic acid is known as the Wittig-Horner-Emmons reaction; this reaction is preferably carried out in the presence of a basic catalyst.

Examples of this basic catalyst include potassium hydroxide, sodium amide, sodium methylate, and potassium t-butoxide. Usable solvents include methyl alcohol, ethyl alcohol, t-butyl alcohol, toluene, tetrahydrofuran, dioxane, dimethyl sulfoxide, and N,N-dimethylformamide. The reaction temperature is generally from room temperature 100° C.

The phosphonic ester represented by formula (8) or (11) described above which may be used as a raw material in the present invention can be easily synthesized by reacting a corresponding halogen compound with a corresponding trialkyl phosphite with heating either directly or in an organic solvent such as toluene, xylene, or N,N-dimethylformamide.

In the case where Ar$_1$ in formula (1) described above is an aryl group having a substituent, examples of the substituent include a lower alkyl group having 1 to 4 carbon atoms, a lower alkoxy group having 1 to 4 carbon atoms, a cycloalkyl group having 5 to 6 carbon atoms, a benzyl group, a phenyl group, and a halogen atom. When the substituent is a lower alkyl group or a lower alkoxy group, it may be further substituted with a lower alkoxy group having 1 to 4 carbon atoms or a halogen atom. When the substituent is a benzyl group or a phenyl group, it may be further substituted with a lower alkyl group having 1 to 4 carbon atoms, a lower alkoxy group having 1 to 4 carbon atoms, or a halogen atom. Examples of the aryl group represented by Ar$_1$ include phenyl, naphthyl, biphenylyl, anthryl, and pyrenyl.

In the case where Ar$_2$ is a phenylene, naphthylene, biphenylene, or anthrylene group each having a substituent, examples of the substituent include a lower alkyl group having 1 to 4 carbon atoms, a lower alkoxy group having 1 to 4 carbon atoms, and a halogen atom. When the substituent is a lower alkyl group or a lower alkoxy group, it may be further substituted with a lower alkoxy group having 1 to 4 carbon atoms or a halogen atom.

In the case where X, Y, or Z is an aryl group having a substituent, examples of the substituent include the same substituents as the aforementioned substituents with which Ar$_1$ can be substituted. In the case where X is an alkyl group having a substituent, examples of the substituent include a lower alkoxy group having 1 to 4 carbon atoms, a cycloalkyl group having 5 to 6 carbon atoms, and a halogen atom. Examples of the aryl group represented by X, Y, or Z include phenyl, naphthyl, biphenylyl, anthryl, and pyrenyl.

Examples of the lower alkyl group represented by R$_1$ include a methyl group, an ethyl group, a propyl group, and a butyl group. Examples of the lower alkoxy group represented by R$_1$ include a methoxy group, an ethoxy group, a propoxy group, and a butoxy group.

The compound of formula (1) of the present invention is exemplified below.

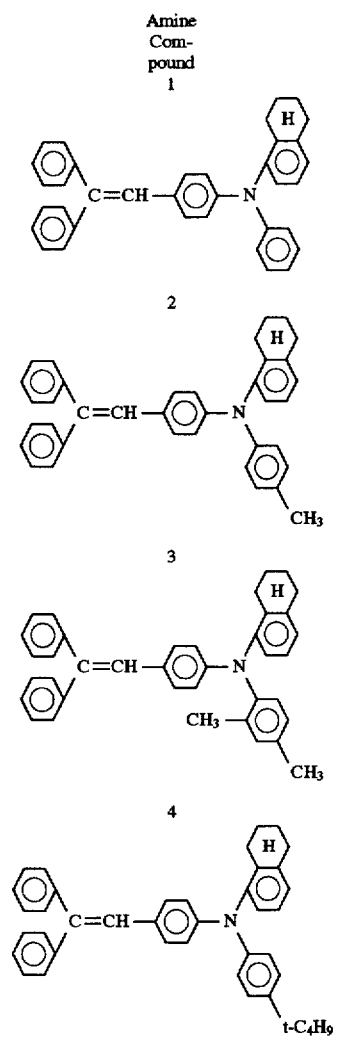

5
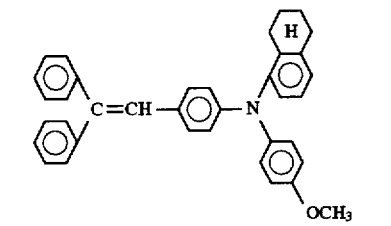
6
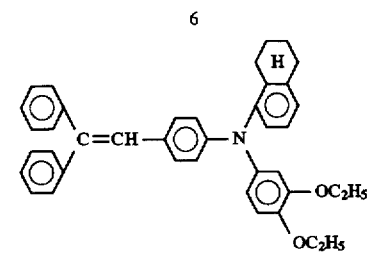
7
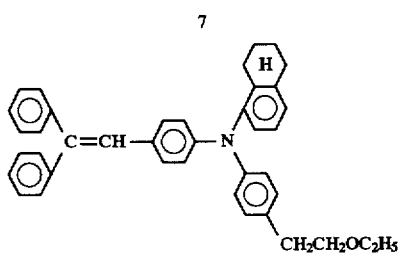
8
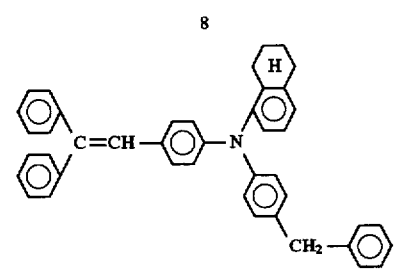
9
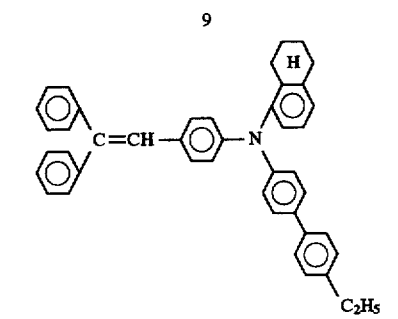
10
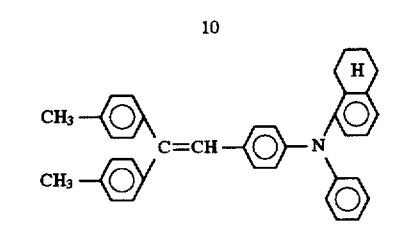
11
12
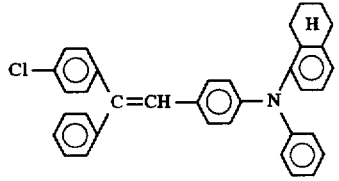
13
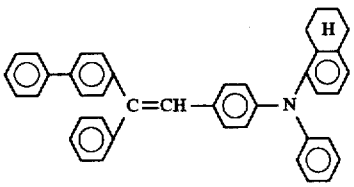
14
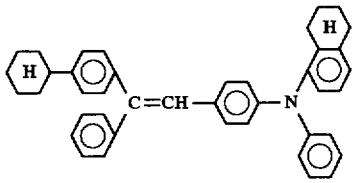
15
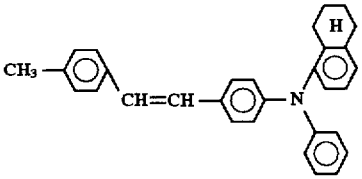
16
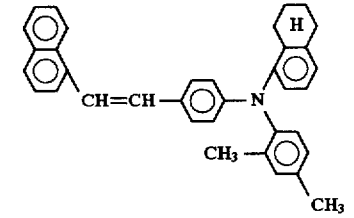
17
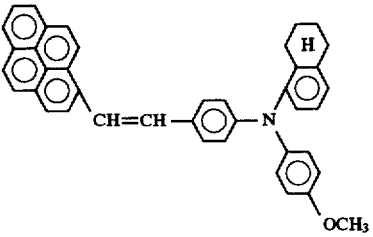
18
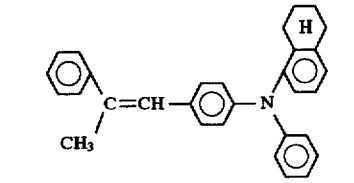

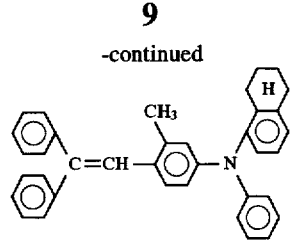
19
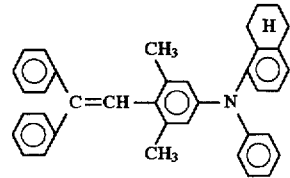
20
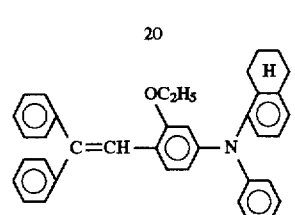
21
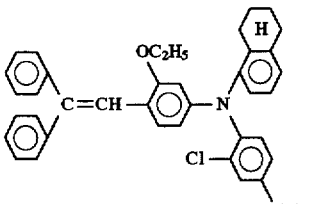
22
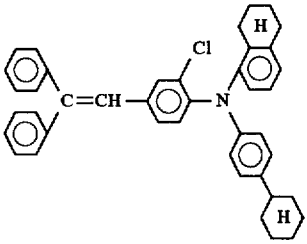
23
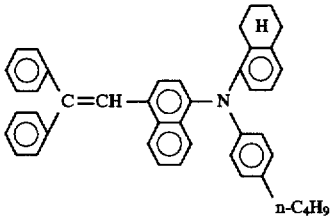
24
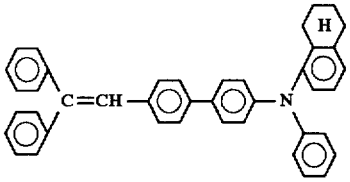
25
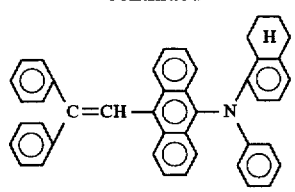
26

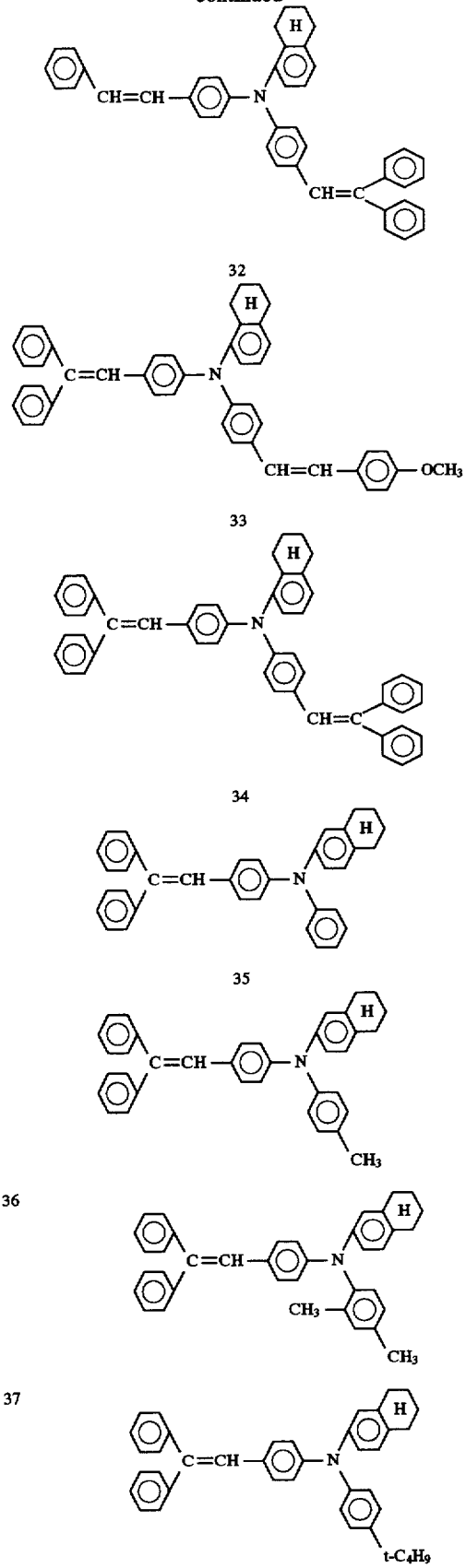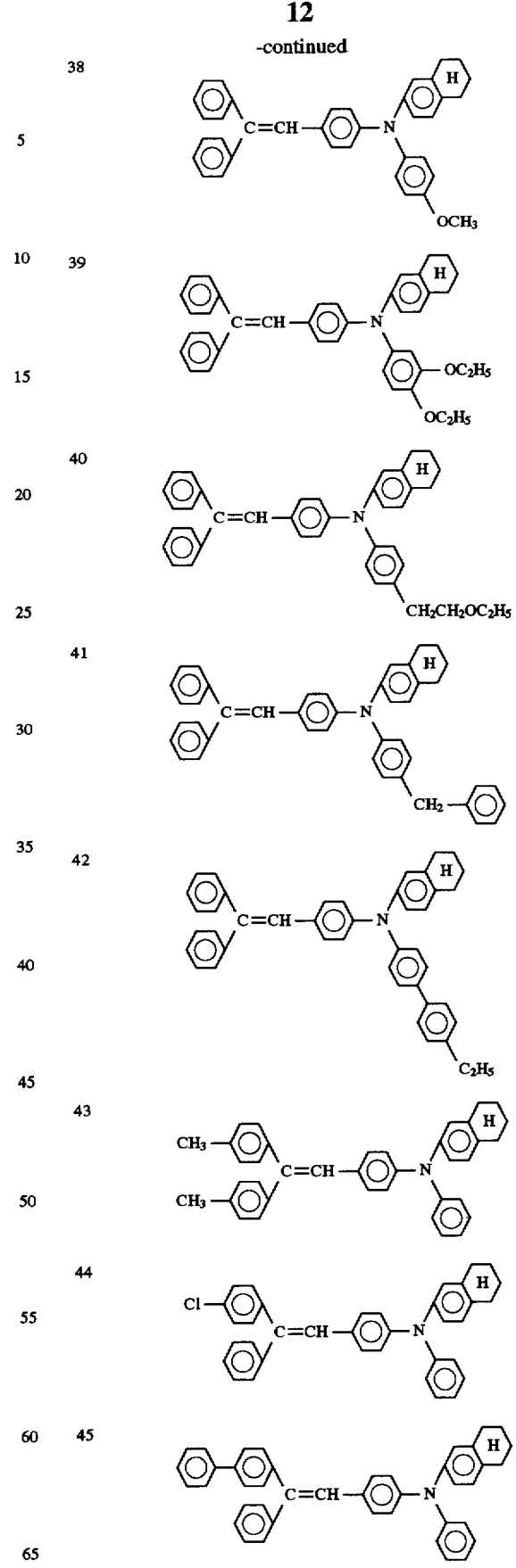

46 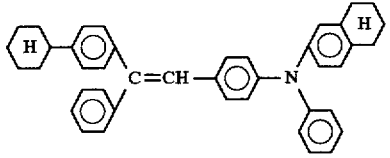
47 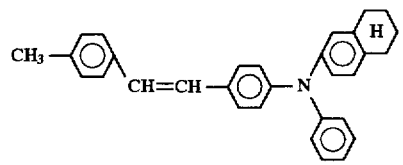
48 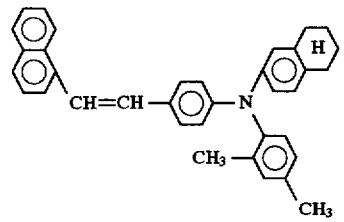
49 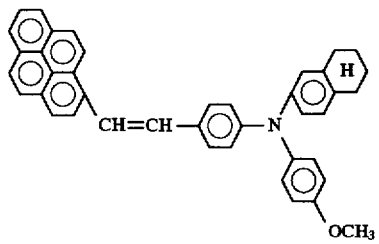
50 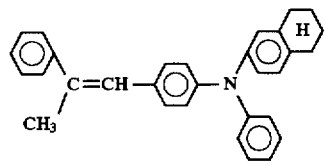
51 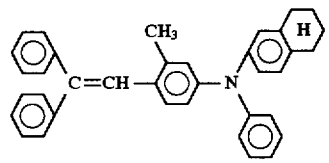
52 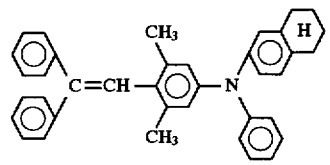
53 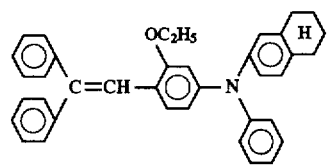
54 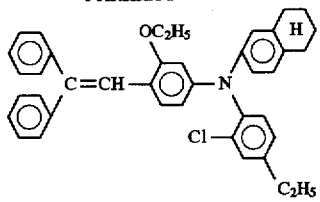
55 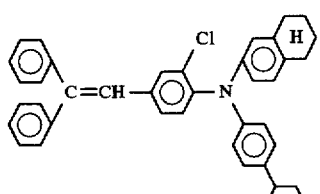
56 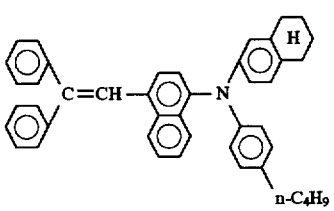
57 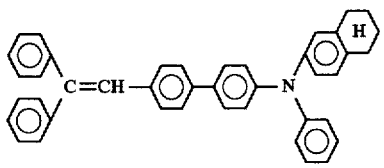
58 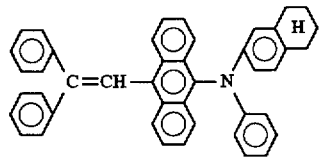
59 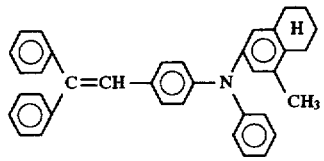
60 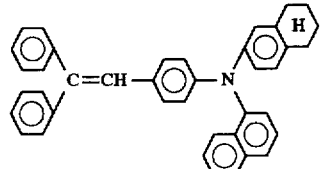
61 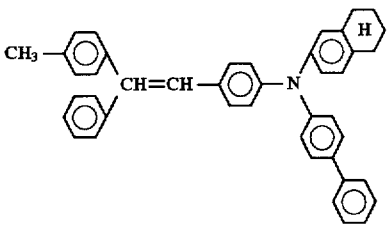

-continued

62 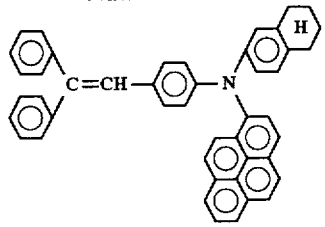

63 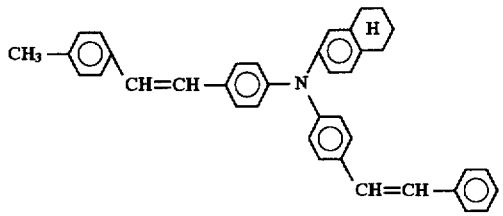

64 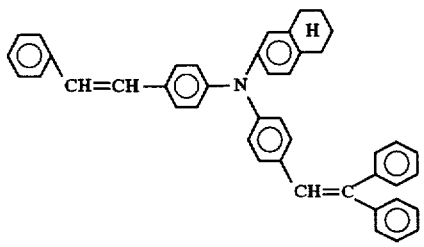

65 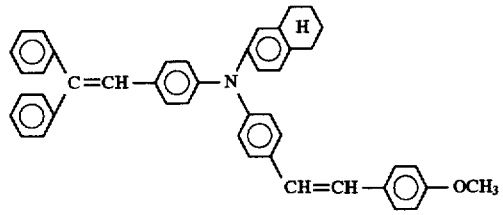

66 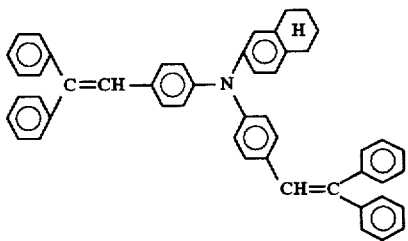

67 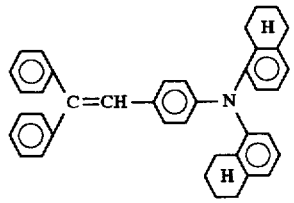

68 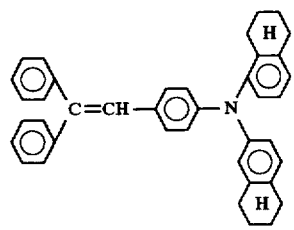

-continued

69 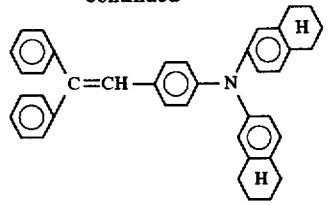

70 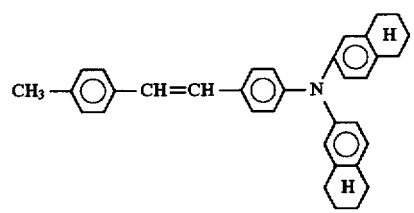

The electrophotographic photoreceptor of the present invention has a photosensitive layer containing one or more amine compounds represented by formula (1). The photosensitive layer of the electrophotographic photoreceptor of the present invention may have any of various possible constitutions. Photoreceptors having representative photosensitive-layer constitutions are shown in FIGS. 1 to 5.

The photoreceptor shown in FIG. 1 comprises a conductive support 1 and formed thereon a photosensitive layer 2 comprising the amine compound, a sensitizing dye, and a binder resin.

Figure 2:
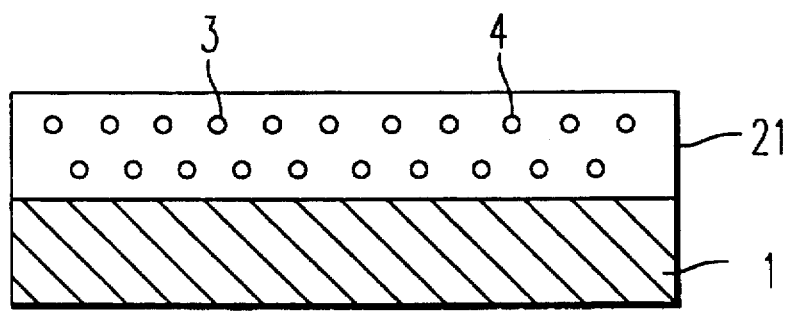
FIG. 2 is a sectional view of a single-layer electrophotographic photoreceptor containing a charge generation material dispersed therein.

The photoreceptor shown in FIG. 2 comprises a conductive support 1 and formed thereon a photosensitive layer 21 comprising a charge-transporting medium 3 comprising the amine compound and a binder resin and a charge generation material 4 dispersed in a charge-transporting medium 3. In this photoreceptor, the charge generation material generates charges upon light absorption and the charges are transported by the charge-transporting medium. It is desirable that the charge transporting material does not absorb the light which the charge generation material absorbs to generate charges. The amine compound shows little light absorption in the visible wavelength region, and therefore satisfies the condition that its absorption wavelength region does not overlap with that of a charge generation material.

In the photoreceptors shown in FIGS. 1 and 2, the thickness of the photosensitive layer is preferably from 10 to 25 μm.

Figure 3:
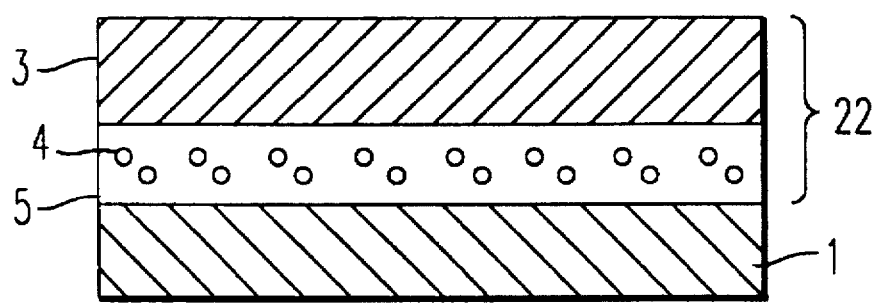
FIG. 3 is a sectional view of an electrophotographic photoreceptor comprising a charge generation layer and a charge transporting layer formed in this order on an electrically conductive support.

The photoreceptor shown in FIG. 3 comprises a conductive support 1 and formed thereon a photosensitive layer 22 made up of a charge generation layer 5 consisting mainly of a charge generation material 4 and a charge transporting layer 3 comprising the amine compound and a binder resin. In this photoreceptor, the light which has passed through the charge transporting layer 3 reaches the charge generation layer 5, where the light is absorbed by the charge generation material 4 to generate charges. These charges are injected into the charge transporting layer 3 and transported.

Figure 4:
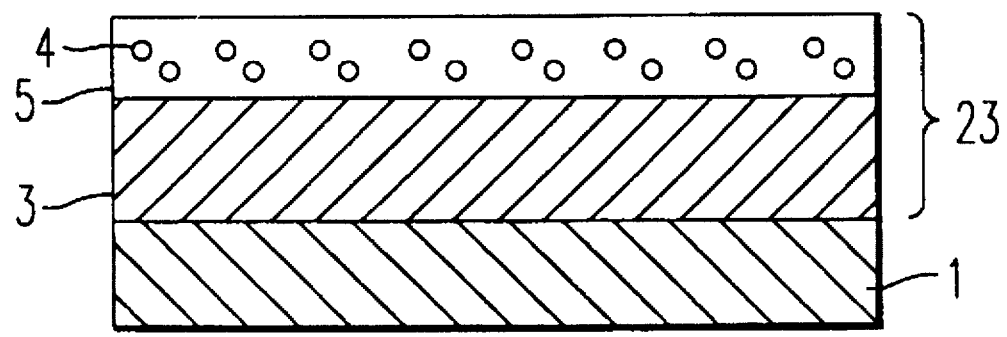
FIG. 4 is a sectional view of an electrophotographic photoreceptor comprising a charge transporting layer and a charge generation layer formed in this order on an electrically conductive support.

The photoreceptor shown in FIG. 4 has a photosensitive layer 23 which is the same as the photosensitive layer of the photoreceptor shown in FIG. 3 except that the positions of the charge generation layer 5 and the charge transporting layer 3 are reversed. The mechanism of charge generation and charge transportation in this photoreceptor is, the same as in the above photoreceptor.

Figure 5:
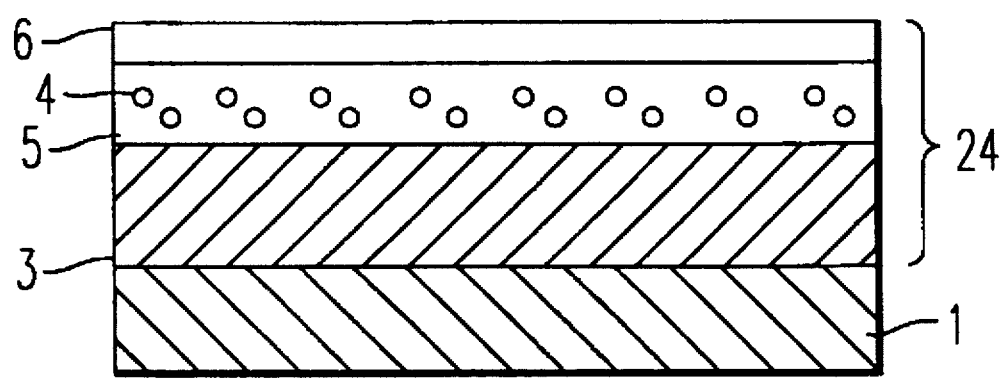
FIG. 5 is a sectional view of an electrophotographic photoreceptor having a protective layer.

The photoreceptor shown in FIG. 5 has a photosensitive layer 24 which is the same as the photosensitive layer of the photoreceptor shown in FIG. 4 except that it further has a protective layer 6 formed on the charge generation layer 5 for the purpose of improving mechanical strength.

In the photoreceptors shown in FIGS. 3, 4 and 5, the thickness of the charge generation layer is preferably 2 µm or less, and the thickness of the charge transporting layer is preferably 5 to 35 µm. The thickness of the protective layer is preferably 2 µm or less.

The amount of the amine compound in the amine compound-containing layer is generally from 30 to 70% by weight, preferably from 40 to 60% by weight.

The amount of the sensitizing dye in the photosensitive layer shown in FIG. 1 is generally from 0.1 to 5% by weight. The amount of the charge generation material in the photosensitive layer shown in FIG. 2 is generally from 1 to 30% by weight. The amount of the charge generation material in the charge generation layers shown in FIGS. 3, 4 and 5 is generally from 20 to 90% by weight. The sensitizing dye and electron-withdrawing compound each can be used generally in an amount of 0.1 to 5% by weight.

These photoreceptors according to the present invention may be produced by ordinary methods. For example, the amine compound represented by formula (1) described above is dissolved in an appropriate solvent along with a binder resin. If desired, a charge generation material, a sensitizing dye, an electron-withdrawing compound, a plasticizer, a pigment, and other additives are added to the solution. The coating fluid thus prepared is applied to a conductive support and dried to form a photosensitive layer having a thickness of several micrometers to tens of micrometers to thereby produce a photoreceptor. A photosensitive layer having a double-layer structure comprising a charge generation layer and a charge transporting layer can be produced by applying the above-described coating fluid on a charge generation layer, or by forming a charge generation layer on a charge transporting layer formed from the above-described coating fluid by coating. If desired, an adhesive layer, an interlayer, or a barrier layer may be formed in the photoreceptors thus produced.

Examples of the charge generation material which can be used in the present invention include any conventional charge generation material such as azo compounds, bisazo compounds, trisazo compounds, tetrakisazo compounds, thiapyrylium salts, squarilium salts, azulenium salts, cyanine dyes, perylene compounds, metal-free or metal phthalocyanine compounds, polynuclear quinone compounds, thioindigo compounds, and quinacridone compounds.

Examples of the solvent which can be used for the preparation of the coating fluid include polar organic solvents such as tetrahydrofuran, 1,4-dioxane, methyl ethyl ketone, cyclohexanone, acetonitrile, N,N-dimethylformamide, and ethyl acetate, aromatic organic solvents such as toluene and xylene, and chlorinated hydrocarbon solvents such as dichloromethane and dichloroethane. Solvents in which the amine compound and the binder resin are highly soluble are preferred.

Examples of the sensitizing dye include triarylmethane dyes such as Methyl Violet, Brilliant Green, Crystal Violet, and Acid Violet, xanthene dyes such as Rhodamine B, Eosine S, and Rose Bengal, thiazine dyes such as Methylene Blue, pyrylium dyes such as benzopyrylium salts, thiapyrylium dyes, and cyanine dyes.

Examples of the electron-withdrawing compound which forms a charge transfer complex in cooperation with the amine compound include quinones, e.g., chloranil, 2,3-dichloro-1,4-naphthoquinone, 1-nitroanthraquinone, 2-chloroanthraquinone, and phenanthrenequinone, aldehydes, e.g., 4-nitrobenzaldehyde, ketones, e.g., 9-benzoylanthracene, indandione, 3,5-dinitrobenzophenone, 2,4,7-trinitrofluorenone, and 2,4,5,7-tetranitrofluorenone, acid anhydrides, e.g., phthalic anhydride and 4-chloronaphthalic anhydride, cyano compounds, e.g., tetracyanoethylene, terephthalalmalenonitrile, and 9-anthrylmethylidenemalenonitrile, and phthalide derivatives, e.g., 3-benzalphthalide and 3-(α-cyano-p-nitrobenzal)-4,5,6,7-tetrachlorophthalide.

Examples of the binder resin include various resins compatible with the amine compound, such as homopolymers and copolymers of vinyl compounds, e.g., styrene, vinyl acetate, vinyl chloride, acrylic esters, methacrylic esters, and butadiene, poly(vinyl acetal)s, polycarbonates, polyesters, poly(phenylene oxide)s, polyurethanes, cellulose esters, phenoxy resins, silicon resins, and epoxy resins. The binder resin is used in an amount of usually from 0.4 to 10 times by weight, preferably from 0.5 to 5 times by weight, the amount of the amine compound.

A known plasticizer may be incorporated into the photosensitive layer of the present invention for the purpose of improving film-forming properties, flexibility, and mechanical strength. Examples of the plasticizer include phthalic esters, phosphoric esters, chlorinated paraffins, methylnaphthalene, epoxy compounds, and chlorinated fatty esters.

The conductive support on which the photosensitive layer is formed may be a material for use as the support of a known electrophotographic photoreceptor. Examples of the support include drums or sheets of a metal, e.g., aluminum, stainless steel, or copper; substrates obtained by laminating or vapor-depositing such a metal; plastic films or drums and paper sheets or tubes to each of which electrical conductivity has been imparted by coating with a conductive substance, e.g., a metal powder, carbon black, copper iodide, or a polymeric electrolyte, along with an appropriate binder; and plastic films or drums to each of which electrical conductivity has been imparted by incorporating such a conductive substance.

The present invention will be explained below in more detail by reference to the following Examples, but the invention should not be construed as being limited thereto. Otherwise indicated, all parts and percentage are by weight.

SYNTHESIS EXAMPLE 1

(Synthesis of Amine Compound No. 1)

Synthesis of Iodotetralin

In 600 ml of 80% acetic acid was dissolved 132.2 g (1.00 mol) of tetralin. To this solution were added 101.5 g (0.40 mol) of iodine, 45.5 g (0.20 mol) of periodic acid dihydrate, and 15 ml of concentrated sulfuric acid. This mixture was heated to 70° C. with stirring and then stirred at this temperature for 3 hours. After disappearance of the tetralin was ascertained, the reaction was terminated. The reaction mixture was added to 1,000 ml of water, and the oily matter separated was extracted with 1,000 ml of toluene. The toluene layer was washed with water, concentrated, and then distilled at a reduced pressure (boiling point: 120° C./3 mmHg). As a result, the main fraction was obtained in an amount of 215.3 g (yield; 83.4%). This reaction product was a 1:2 mixture of 5-iodotetralin and 6-iodotetralin.

Synthesis of N-(1,2,3,4-Tetrahydronaphtho-5-yl)aniline

The iodotetralin mixture synthesized above was mixed in an amount of 171.0 g (0.66 mol) with 81.0 g (0.60 mol) of acetanilide, 3.8 g (0.06 mol) of a copper powder, and 103.5 g (0.75 mol) of anhydrous potassium carbonate. This mixture was stirred at 200° C. for 8 hours. The reaction was terminated after disappearance of the acetanilide was ascertained. To the reaction mixture were added 120 ml of isoamyl alcohol and an aqueous solution obtained by dissolving 84 g (1.27 mol) of 85% potassium hydroxide in 160 ml of water. Hydrolysis was then conducted at 130° to 140° C. for 10 hours. After termination of the hydrolysis reaction was ascertained, 600 ml of water was added and the isoamyl alcohol was removed by azeotropic distillation. To the residue was added 1,000 ml of toluene to dissolve a reaction product. The toluene layer was separated, washed with 500 ml of water, and then concentrated. The thus-obtained oily matter was subjected to column chromatography (carrier; silica gel, eluent; toluene/hexane=1/1 by volume) to separate the mixture into components and purify the reaction product. The fraction containing N-(1,2,3,4-tetrahydronaphtho-5-yl)aniline was concentrated to obtain 30.9 g (yield; 23.1%) of N-(1,2,3,4-tetrahydronaphtho-5-yl)aniline.

Synthesis of N-(1,2,3,4-Tetrahydronaphtho-5-yl) diphenylamine 22.3 g (0.10 mol) of N-(1,2,3,4-tetrahydronaphtho-5-yl)aniline synthesized above was mixed with 30.6 g (0.15 mol) of iodobenzene, 0.65 g (0.01 mol) of a copper powder, and 13.8 g (0.10 mol) of anhydrous potassium carbonate. This mixture was stirred at 200° C. for 18 hours. After disappearance of the N-(1,2,3,4-tetrahydronaphtho-5-yl)aniline was ascertained, the reaction was terminated. To the reaction mixture was added 300 ml of toluene to dissolve a reaction product. The resulting mixture was filtered, and the filtrate was concentrated. The concentrate was purified by column chromatography (carrier; silica gel, eluent; toluene/hexane= 1/5 by volume) to obtain 23.6 g (yield; 78.8%), melting point; 89.5°–90.5° C.) of N-(1,2,3,4-tetrahydronaphtho-5-yl)diphenylamine.

Synthesis of N-(1,2,3,4-Tetrahydronaphtho-5-yl)-4-formyldiphenylamine

In 170 ml of N,N-dimethylformamide was dissolved 18.0 g (0.06 mol) of the N-(1,2,3,4-tetrahydronaphtho-5-yl)diphenylamine synthesized above. To this solution was added dropwise 13.1 g (0.085 mol) of phosphorus oxychloride at room temperature over a period of 15 minutes. This mixture was heated to 50° C. and stirred for 10 hours. After disappearance of the N-(1,2,3,4-tetrahydronaphtho-5-yl)diphenylamine was ascertained, the reaction was terminated. The reaction mixture was then poured into an aqueous solution obtained by dissolving 25 g (0.58 mol) of 93% sodium hydroxide in 500 ml of water. The resulting mixture was cooled to precipitate crystals, which were then separated by filtration, washed with water, and dried to obtain 18.1 g (yield; 92.1%) of N-(1,2,3,4-tetrahydronaphtho-5-yl)-4-formyldiphenylamine.

Synthesis of N-(1,2,3,4-Tetrahydronaphtho-5-yl)-4-(2,2-diphenylvinyl)diphenylamine (Amine Compound No. 1)

In 180 ml of tetrahydrofuran were dissolved 16.4 g (0.05 mol) of the N-(1,2,3,4-tetrahydronaphtho-5-yl)-4-formyldiphenylamine synthesized above and 22.8 g (0.075 mol) of diethyl diphenylmethylphosphonate. To this solution was added 10.5 g (0.094 mol) of potassium t-butoxide at room temperature over a period of 30 minutes. The mixture was then heated to 50° C. and stirred for 2 hours. After disappearance of the formyl compound was ascertained, the reaction was terminated. The reaction mixture was poured into 900 ml of methanol at 5° C. or lower, and the crystals precipitated were separated by filtration, washed with methanol, washed with water, and then dried. The dried crystals were purified by column chromatography (carrier; silica gel, eluent; toluene/hexane=1/4 by volume) to obtain 20.4 g (yield; 85.3%, melting point; 139.0°–140.5° C.) of N-(1,2,3,4-tetrahydronaphtho-5-yl)-4-(2,2-diphenylvinyl)diphenylamine (Amine Compound No. 1).

Results of elemental analysis are as follows (the theoretical values calculated for $C_{36}H_{31}N$ are shown in the parentheses). Carbon: 90.39% (90.53%), hydrogen: 6.75% (6.54%), nitrogen: 2.71% (2.93%).

An infrared absorption spectrum thereof (KBr tablet method) had absorption peaks assigned to characteristic groups at wavenumber ($cm^{-1}$) of 2922, 1587, 1490, 1307, etc.

EXAMPLE 1

To 18.5 parts of an 8% THF solution of a polyester resin (Vylon 200, manufactured by Toyobo Co., Ltd., Japan) was added, as a charge generation material, 1.5 parts of Chlorodiane Blue (hereinafter Compound A) having the following structure.

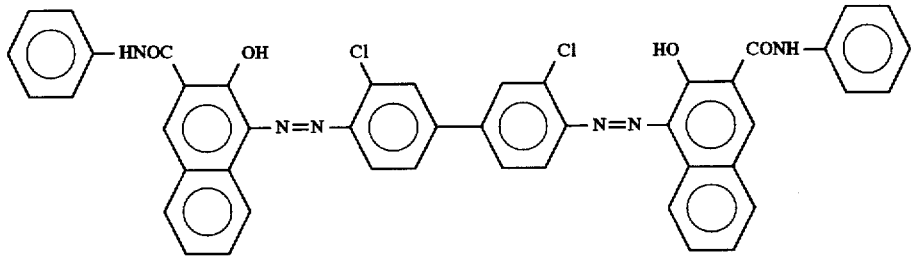

This mixture was placed in an agate pot containing agate balls, and this pot was rotated for 1 hours in a planetary grinder (manufactured by Fritsch Co.) to disperse the charge generation material. An aluminum-deposited PET film serving as a conductive support was coated on the aluminum side with the above-obtained dispersion by means of a wire-wound bar coater. The coating was dried first at 60° C. and ordinary pressure for 2 hours and then at reduced pressure for 2 hours to form a charge generation layer having a thickness of 0.3 μm.

On the other hand, 1.5 parts of Amine Compound No. 1 as a charge transporting material was added to 18.75 parts of an 8% dichloroethane solution of a polycarbonate resin (Panlite K-1300, manufactured by Teijin Chemicals Ltd., Japan). Ultrasonic wave was applied to this mixture to completely dissolve the amine compound. This solution was applied to the charge generation layer with a wire-wound bar coater, and the coating was dried first at 60° C. and ordinary pressure for 2 hours and then at reduced pressure for 2 hours to form a charge transporting layer having a thickness of about 20 μm. Thus, photoreceptor No. 1 was produced.

The sensitivity of this photoreceptor was measured with an electrostatic copying paper tester (trade name "EPA- 8100," manufactured by Kawaguchi Denki Seisakusho K.K., Japan) as follows. First, the photoreceptor was charged in the dark with −8 kV corona discharge. The resulting photoreceptor was exposed to white light at 3.0 lx to measure the time (sec) required for the surface potential to decrease to a half of the initial surface potential value. Thus, the half decay exposure, $E_{1/2}$ (lx·sec), was determined. This photoreceptor had an initial surface potential of −1,020 V and an $E_{1/2}$ of 0.81 lx·sec.

EXAMPLE 2 TO 29

Photoreceptor Nos. 2 to 29 were produced in the same manner as in Example 1, except that the charge generation material (Compound A, B, C and D) and charge transporting material (amine compound) were changed as shown in Table 1.

The results of the evaluation of photoreceptor Nos. 2 to 29 are given in Table 2.

TABLE 1

| Example No. | Photoreceptor No. | Charge Transporting Material Compound No. | Charge Generation Material Compound No. |
|---|---|---|---|
| 2 | 2 | 2 | C |
| 3 | 3 | 3 | A |
| 4 | 4 | 5 | A |
| 5 | 5 | 10 | A |
| 6 | 6 | 14 | B |
| 7 | 7 | 16 | B |
| 8 | 8 | 18 | B |
| 9 | 9 | 20 | B |
| 10 | 10 | 23 | A |
| 11 | 11 | 25 | C |
| 12 | 12 | 29 | C |
| 13 | 13 | 32 | D |
| 14 | 14 | 33 | D |
| 15 | 15 | 34 | A |
| 16 | 16 | 35 | C |
| 17 | 17 | 36 | A |
| 18 | 18 | 38 | A |
| 19 | 19 | 43 | A |
| 20 | 20 | 47 | B |
| 21 | 21 | 49 | B |
| 22 | 22 | 51 | B |
| 23 | 23 | 53 | B |
| 24 | 24 | 56 | A |
| 25 | 25 | 58 | C |
| 26 | 26 | 62 | C |
| 27 | 27 | 65 | D |
| 28 | 28 | 66 | D |
| 29 | 29 | 68 | C |

TABLE 2

| Photoreceptor No. | Initial Surface Potential (−V) | $E_{1/2}$ (lx · sec) |
|---|---|---|
| 2 | 1026 | 0.87 |
| 3 | 1035 | 0.84 |
| 4 | 985 | 0.90 |
| 5 | 1007 | 1.03 |
| 6 | 962 | 1.07 |
| 7 | 971 | 0.89 |
| 8 | 994 | 0.92 |
| 9 | 980 | 0.95 |
| 10 | 1004 | 1.15 |
| 11 | 1010 | 1.04 |
| 12 | 946 | 0.78 |
| 13 | 988 | 0.85 |
| 14 | 963 | 0.82 |
| 15 | 1016 | 0.84 |
| 16 | 952 | 0.85 |
| 17 | 974 | 0.89 |
| 18 | 988 | 0.94 |
| 19 | 942 | 1.02 |
| 20 | 1025 | 1.06 |
| 21 | 969 | 0.86 |
| 22 | 965 | 0.96 |
| 23 | 918 | 0.94 |
| 24 | 1013 | 1.11 |
| 25 | 1024 | 1.01 |
| 26 | 886 | 0.80 |
| 27 | 1048 | 0.86 |
| 28 | 990 | 0.85 |
| 29 | 951 | 1.07 |

The same as Compound A used in Example 1.    Compound A

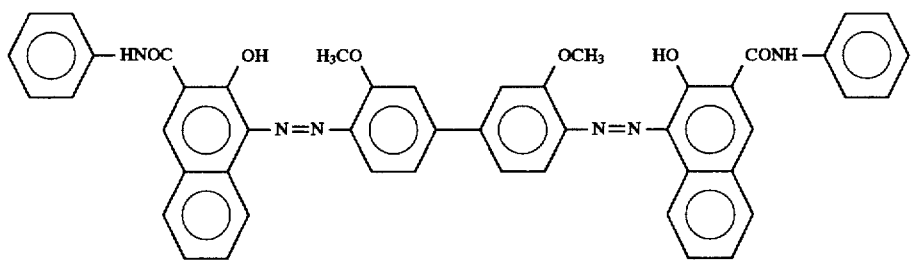

Compound B

-continued

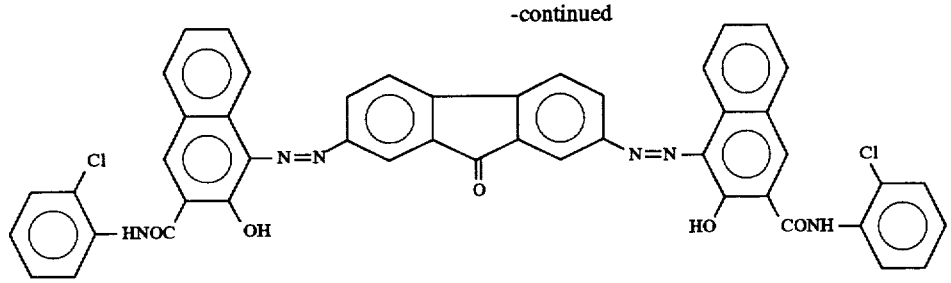

Compound C

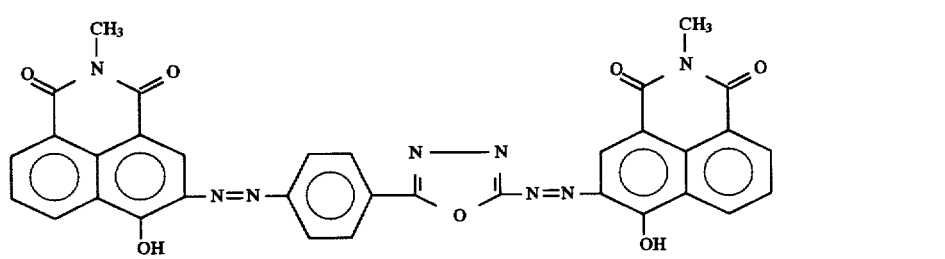

Compound D

EXAMPLE 30

Photoreceptor No. 30 was produced in the same manner as in Example 1, except that a mixture (1:1 by weight) of Amine Compound Nos. 1 and 34 was used in place of Amine Compound No. 1 used as a charge transporting material.

The sensitivity of this photoreceptor was measured in the same manner as in Example 1. As a result, this photoreceptor had an initial surface potential of −1,067 V and an $E_{1/2}$ of 0.78 lx·sec.

EXAMPLE 31

To 50 parts of a 3% THF solution of a poly(vinyl butyral) resin (S-Lec BX-L, manufactured by Sekisui Chemical Co., Ltd., Japan) was added 1.5 parts of α-TiOPc as a charge generation material. This mixture was treated with an ultrasonic dispersing machine for 45 minutes to obtain a dispersion. An aluminum-deposited PET film serving as a conductive support was coated on the aluminum side with the above-obtained dispersion by means of a wire-wound bar coater. The coating was dried first at 60° C. and ordinary pressure for 2 hours and then at reduced pressure for 2 hours to form a charge generation layer having a thickness of 0.2 μm.

On the other hand, 1.5 parts of Amine Compound No. 1 as a charge transporting material was added to 18.75 parts of an 8% dichloroethane solution of a polycarbonate resin (Panlite K-1300, manufactured by Teijin Chemicals Ltd.). Ultrasonic wave was applied to this mixture to completely dissolve the amine compound.

This solution was applied to the charge generation layer with a wire-wound bar coater, and the coating was dried first at 60° C. and ordinary pressure for 2 hours and then at reduced pressure for 2 hours to form a charge transporting layer having a thickness of about 20 μm. Thus, photoreceptor No. 31 was produced.

The sensitivity of this photoreceptor was measured with an electrostatic copying paper tester (trade name "EPA-8100") as follows. First, the photoreceptor was charged in the dark with −8 kV corona discharge. The resulting photoreceptor was exposed to 800-nm monochromatic light at a light quantity of 1.0 μW/cm² to measure the quantity of energy required for the surface potential to decrease to a half of the initial surface potential value. Thus, the half decay exposure, $E_{1/2}$ (μJ/cm²), was determined. This photoreceptor had an initial surface potential of −964 V and an $E_{1/2}$ of 0.45 μJ/cm².

EXAMPLE 32

Photoreceptor No. 32 was produced in the same manner as in Example 31, except that the following trisazo compound was used as a charge generation material in place of α-TiOPc.

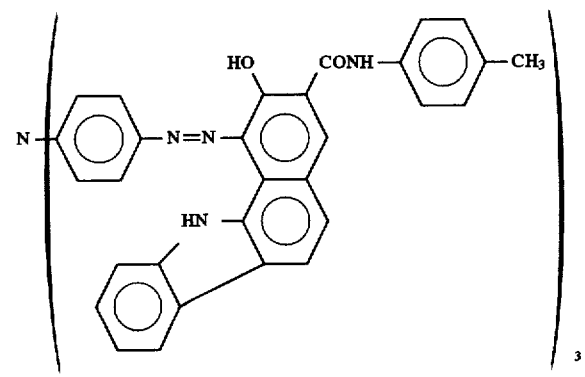

The sensitivity of this photoreceptor was measured in the same manner as in Example 31. As a result, this photoreceptor was found to have an initial surface potential of −1,025 V and an $E_{1/2}$ of 0.43 μJ/cm².

EXAMPLE 33

To 125 parts of an 8% dichloroethane solution of a polycarbonate resin (Panlite K-1300, manufactured by Teijin Chemicals Ltd.) were added 0.1 part of the following thiapyrylium salt as a charge generation material

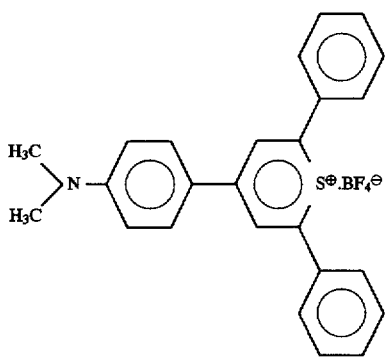

and 10 parts of Amine Compound No. 35 as a charge transporting layer. Ultrasonic wave was applied to this mixture to completely dissolve the thiapyrylium salt and the amine compound. An aluminum-deposited PET film serving as a conductive support was coated on the aluminum side with the above-obtained solution by means of a wire-wound bar coater. The coating was dried first at 60° C. and ordinary pressure for 2 hours and then at reduced pressure for 2 hours to form a photosensitive layer having a thickness of 20 μm. Thus, photoreceptor No. 33 was produced.

The sensitivity of this photoreceptor was measured with an electrostatic copying paper tester (trade name "EPA-8100") as follows. First, the photoreceptor was charged in the dark with +8 kV corona discharge. The resulting photoreceptor was exposed to white light at 3.0 lx to measure the time (sec) required for the surface potential to decrease to a half of the initial surface potential value. Thus, the half decay exposure, $E_{1/2}$ (lx·sec), was determined. This photoreceptor had an initial surface potential of +986 V and an $E_{1/2}$ of 1.3 lx·sec.

EXAMPLE 34

An aluminum-deposited PET film was coated on the aluminum side with the coating solution of a charge transporting material which solution had been used in Example 1, by means of a wire-wound bar coater. The coating was dried first at 60° C. and ordinary pressure for 2 hours and then at reduced pressure for 2 hours to form a charge transporting layer having a thickness of 10 μm.

On the other hand,3.0 parts of the same disazo compound as used in Example 2 was added as a charge generation material to 18.5 parts of an 8% THF solution of a polyester resin (Vylon 200, manufactured by Toyobo Co., Ltd.). This mixture was placed in an agate pot containing agate balls, and this pot was rotated for 1 hours in a planetary grinder (manufactured by Fritsch Co.) to disperse the charge generation material. To this dispersion was added 200 parts of THF. The resulting mixture was stirred to give a coating fluid, which was then applied to the charge transporting layer by spraying. The coating was dried first at 60° C. and ordinary pressure for 2 hours and then at reduced pressure for 2 hours to form a charge generation layer having a thickness of 0.5 μm. This charge generation layer was further coated by spraying with a solution obtained by dissolving an alcohol-soluble polyamide resin in isopropanol. The coating was dried first at 60° C. and ordinary pressure for 2 hours and then at reduced pressure for 2 hours to form an overcoat layer having a thickness of 0.5 μm. Thus, photoreceptor No. 34 was produced.

The sensitivity of this photoreceptor was measured in the same manner as in Example 1. As a result, this photoreceptor was found to have an initial surface potential of +840 V and an $E_{1/2}$ of 1.1 lx·sec.

The novel amine compound of the present invention has excellent charge-transporting ability, and the electrophotographic photoreceptor of the present invention having a photosensitive layer containing the amine compound on a conductive support shows excellent photoreceptor properties such as high sensitivity and high durability and can be advantageously utilized widely as an electrophotographic photoreceptor.

While the invention has been described in detail and with reference to specific embodiments thereof, it will be apparent to one skilled in the art that various changes and modifications can be made therein without departing from the spirit and scope thereof.

What is claimed is:

1. An electrophotographic photoreceptor having a photosensitive layer containing a sensitizing dye or charge generation material, a binder resin and at least one amine compound represented by formula (1):

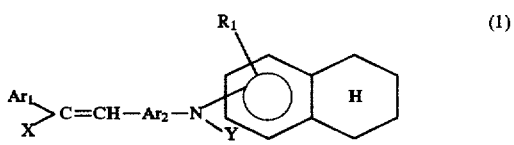

wherein $Ar_1$ represents a substituted or unsubstituted aryl group, $Ar_2$ represents a substituted or unsubstituted phenylene group, a substituted or unsubstituted naphthylene group, a substituted or unsubstituted biphenylene group or a substituted or unsubstituted anthrylene group, $R_1$ represents a hydrogen atom, a lower alkyl group or lower alkoxy group, X represents a hydrogen atom, a substituted or unsubstituted alkyl group, or a substituted or unsubstituted aryl group, Y represents a substituted or unsubstituted aryl group a substituent being selected from the group consisting of lower alkyl groups having 1–4 carbon atoms, lower alkoxy groups having 1–4 carbon atoms, cycloalkyl groups having 5–6 carbon atoms, a benzyl group, a phenyl group, halogen, lower alkyl groups having 1–4 carbon atoms substituted with a lower alkoxy group having 1–4 carbon atoms or a halogen, lower alkoxy groups having 1–4 carbon atoms substituted with a lower alkoxy group having 1–4 carbon atoms or a halogen, benzyl groups substituted with a lower alkyl group having 1–4 carbon atoms, a lower alkoxy group having 1–4 carbon atoms or a halogen, and phenyl groups substituted with a lower alkyl group having 1–4 carbon atoms, a lower alkoxy group having 1–4 carbon atoms or a halogen, or a group represented by formula (2):

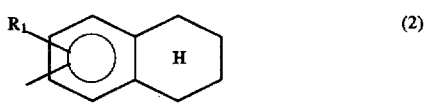

wherein $R_1$ is as defined above.

2. The electrophotographic photoreceptor of claim 1, wherein the amount of the binder resin is 0.4 to 10 times by weight of the amine compound.

3. The electrophotographic photoreceptor of claim 2, wherein the amount of the binder resin is 0.5 to 5 times by weight of the amine compound.

4. The electrophotographic photoreceptor of claim 1, wherein the photosensitive layer contains 30–70% by weight of the amine compound.

5. The electrophotographic photoreceptor of claim 4, wherein the photosensitive layer contains 40–60% by weight of the amine compound.

6. The electrophotographic photoreceptor of claim 1, wherein the photosensitive layer comprises a single layer containing the amine compound, the sensitizing dye and the binder resin.

7. The electrophotographic photoreceptor of claim 6, wherein the photosensitive layer contains 0.1–5% by weight of the sensitizing dye.

8. The electrophotographic photoreceptor of claim 1, wherein the photosensitive layer comprises a single layer containing the amine compound, the binder resin and the charge generation material.

9. The electrophotographic photoreceptor of claim 8, wherein the photosensitive layer contains 1–30% by weight of the charge generation material.

10. The electrophotographic photo receptor of claim 1, wherein the photo-sensitive layer comprises a charge generation layer and a charge transporting layer and wherein the charge generation layer comprises 20–90% by weight of the charge generation material.

* * * * *